US00PP19764P3

(12) United States Plant Patent
Ballington et al.

(10) Patent No.: US PP19,764 P3
(45) Date of Patent: Feb. 24, 2009

(54) BLUEBERRY NAMED 'BEAUFORT'

(50) Latin Name: *Vaccinium corymbosum*
Varietal Denomination: Beaufort

(75) Inventors: James Ralph Ballington, Cary, NC (US); Susan Duke Rooks, Rocky Point, NC (US)

(73) Assignee: North Carolina Agriculture Research Service, Raleigh, NC (US)

( * ) Notice: Subject to any disclaimer, the term of this patent is extended or adjusted under 35 U.S.C. 154(b) by 413 days.

(21) Appl. No.: 11/303,719

(22) Filed: Dec. 19, 2005

(65) Prior Publication Data

US 2007/0143889 P1 Jun. 21, 2007

(51) Int. Cl.
*A01H 5/00* (2006.01)

(52) U.S. Cl. ..... Plt./157

(58) Field of Classification Search ..... Plt./157
See application file for complete search history.

*Primary Examiner*—Annette H Para
*Assistant Examiner*—Georgia Helmer

(57) ABSTRACT

*Vaccinium corymbosum* Linnaeus 'Beaufort' is a new and distinct variety of blueberry plant that has the following unique combination of desirable features that are outstanding in a new variety.

1. Late midseason ripening, extending the harvest season for fresh market mechanical harvest adapted varieties.
2. Consistent high yields of small to medium size fruit.
3. Very good fruit color, firmness and quality, and a good picking scar.
4. Adaptation to mechanical harvesting for fresh fruit market outlets.

2 Drawing Sheets

Latin name of the genus and species: The Latin name of the novel blueberry plant variety disclosed herein is *Vaccinium corymbosum* Linnaeus.

Variety denomination: The inventive cultivar of *Vaccinium corymbosum* plant disclosed herein has been given the variety denomination 'Beaufort'.

BACKGROUND OF THE INVENTION

The present invention relates to a new and distinct cultivar of *Vaccinium corymbosum* Linnaeus (blueberry plant) grown as a fruiting woody shrub for commercial agriculture. Blueberries are typically consumed both fresh and in a number of processed products.

The new and distinct variety of blueberry plant (*Vaccinium corymbosum* Linnaeus) originated from the hand pollinated cross of 'NC 1406' (unpatented)×'Pender' (unpatented) made in 1980 in Raleigh, N.C.

Seeds from this hand pollination were germinated in winter 1980/1981 in Raleigh, N.C., and 250 seedlings were established at Castle Hayne, N.C., in 1982. When the seedlings reached maturity in 1987, an elite genotype designated as 'NC 2901' was selected for its vigorous erect plant habit, productivity, color, picking scar, firmness, quality and late midseason maturity by James R. Ballington. The cross from which 'NC 2901' was selected was specifically made with adaptation to mechanical harvesting for fresh market outlets in mind. 'NC 2901' also possessed another attribute essential for adaptation to mechanical harvest for the fresh market, small to medium fruit size. Three additional cultivars from this cross were previously released in 2004. These are 'Craven' (early ripening) (unpatented), 'Pamlico' (early midseason ripening) (unpatented) and 'Lenoir' (early midseason to midseason ripening) (unpatented).

During 1988 the original seedling of 'NC 2901' was propagated by hardwood stem cuttings at Castle Hayne, N.C., and following rooting, single three plant plots were established at Castle Hayne, Jackson Springs and Fletcher, N.C., in 1989. Based on its performance in these initial trials, in 1996 it was propagated again by hardwood stem cuttings at Castle Hayne and established in replicated trials at Castle Hayne. It was also established in grower trials at Harrells, Ivanhoe, Rocky Point and White Lake, N.C., and at Clarksville, Ark., in 2001, all under Memoranda of Agreements whereby the growers provided the land and care of the plants and North Carolina State University retained ownership of the variety. Plants and fruit of this new variety have remained true to type through these successive cycles of asexual propagation. This new variety has been named the 'Beaufort' cultivar.

SUMMARY OF THE INVENTION

'Beaufort' is a new and distinct variety of blueberry plant that differs from its female parent, 'NC 1406' (no longer extant in the USA), primarily for picking scar. The picking scar of 'Beaufort' was quite good, while it was unacceptably large for 'NC 1406', and was the primary reason 'NC 1406' was not named as a new cultivar. 'Beaufort' differs from its male parent 'Pender' for fruit firmness, plant vigor, and self-fertility. 'Pender' was released in 1997 for mechanical harvest for the fresh market. However, since its release the fruit has proven to be too soft for the fresh market following mechanical harvesting. 'Beaufort' produces fruit that is much firmer than 'Pender', the 'Beaufort' plant is much more vigorous than 'Pender', and 'Beaufort' flowers are not self-fertile, while those of 'Pender' are fully self-fertile.

'Beaufort' is late midseason ripening and adapted to mechanical harvest for the fresh market, and extends the harvest season for fresh market mechanical harvest adapted varieties beyond that available with previously released varieties. It has high yield potential, higher than 'Reveille' and similar to its siblings 'Lenoir' and 'Pamlico', but not as high as 'Carteret'; very good fruit quality; fruit color superior to 'Lenoir', equal to 'Carteret' and 'Reveille', but not as good as 'Pamlico'; a good picking scar; fruit firmness superior to 'Carteret' and 'Pamlico', and equal to 'Lenoir', but not as good as 'Reveille'; and, modest fruit size which is a requirement for adaptation to mechanical harvest for the fresh market in North Carolina. Fruit firmness of 'Beaufort' was quite sufficient for mechanical harvest for the fresh market. Post harvest shelf-life was adequate when stored at 50° F. for seven days, but was not quite as good as the other varieties with which it was compared. Based on plant height, mature cane diameter, mature cane length, and internode length on first flush growth, plants of 'Beaufort', and the other four cultivars are all vigorous. The plant habit of 'Beaufort' is upright. Leaves are narrowly elliptic in shape and both the leaf base and apex angles acute. The flowers are not self-fertile but produce abundant pollen for pollinator varieties interplanted with 'Beaufort'. 'Beaufort' averaged 3.0 flowers per inflorescence, and the corolla of individual flowers is white and cylindro-urceolate in shape. The fruit is round-oblate in shape and the calyx not prominent and appressed to the apex of the fruit. 'Beaufort' is readily asexually propagated by either softwood or hardwood stem cuttings. It has not had any problems to date with either stem canker or stem blight, the two major diseases of commercial blueberries in North Carolina. The chilling requirement of flower and leaf buds of 'Beaufort' plants is between 600 and 800 hours below 45° F.

With regard to consistent differences between 'Beaufort' and all four of the other varieties with which it was compared, it is later ripening. It was also the only variety in these comparisons where the stem color on the unexposed side (side away from the sun) was yellow-orange, compared to either red or yellow-green for the other four. The average number of flowers per inflorescence for 'Beaufort' was 3.0, while it was 4.0 for 'Pamlico' and 'Reveille', 5.0 for 'Lenoir', and 5.5 for 'Carteret'. The color of the corolla of individual flowers of 'Beaufort' was white just prior to opening, while it was red-purple on all or basal portions of the corolla just prior to opening with the other four cultivars to which it was compared. The numbers of fully developed seeds per berry for 'Beaufort' were higher than for 'Carteret', 'Lenoir', 'Pamlico' or 'Reveille'.

BRIEF DESCRIPTION OF THE DRAWINGS

The photographs in the drawings were made using digital photography techniques, and illustrates the colors as true as reasonably possible when using these techniques. Colors in the photographs may differ slightly from the color values cited in the detailed botanical description, which accurately describe the colors of the new *Vaccinium corymbosum* variety. All photographs were taken from nine year old plants growing Castle Hayne, N.C.

FIG. 1 shows the typical plant habit of 'Beaufort'.

FIG. 2 shows the typical fruit of 'Beaufort'.

DETAILED BOTANICAL DESCRIPTION OF THE VARIETY

The following is a detailed botanical description of a new and distinct variety of *Vaccinium corymbosum* Linnaeus plant known as 'Beaufort'. The observations below are from mature plants grown in test plots at a standard commercial spacing of 4' between plants in rows and 10' between rows, at Castle Hayne, N.C. Those skilled in the art of cultivar description and evaluation will appreciate that certain characteristics of a variety will vary with older or, conversely, with younger plants. 'Beaufort' has not been observed under all possible environmental conditions. Where dimensions, sizes, colors and other characteristics are given, it is to be understood that such characteristics are approximations or averages set forth as accurately as practicable. The phenotype of the variety may differ from the descriptions herein with variations in the environment such as season, temperature, light intensity, day length and cultural conditions. Color notations are based on The Royal Horticultural Society Colour Chart, The Royal Horticultural Society, London, UK, 1995 edition.

For botanical description purposes, 'Beaufort' was compared to the very early ripening fresh market mechanical harvest adapted cultivar 'Reveille' (unpatented) and to three recent fresh market mechanical harvest adapted cultivars, 'Carteret' (Plant Patent applied for), 'Lenoir' and 'Pamlico'. The botanical descriptive data presented are averages of data collected from mature nine year old plants growing in a replicated trial at Castle Hayne, N.C., in 2005. The exception to using average values was with seed numbers where these were determined from a representative fruit of each cultivar.

Plant:

*Dimensions.*—'Beaufort' — 1.4 m height, 1.1 m diameter, H/D ratio 1.27. 'Reveille' — 1.4 m height, 1.2 m diameter, H/D ratio 1.17. 'Pamlico' — 1.3 m height, 1.2 m diameter, H/D ratio 1.08. 'Lenoir' — 1.4 m height, 1.2 m diameter, H/D ratio 1.17. 'Carteret' — 1.4 m height, 1.1 m diameter, H/D ratio 1.27.

*Growth habit.*—Upright for 'Beaufort' (FIG. 1), 'Reveille', 'Lenoir' and 'Carteret'. Semi-upright for 'Pamlico'.

*Vigor.*—Very good for 'Beaufort', 'Reveille' and 'Carteret'. Good for 'Pamlico' and 'Lenoir'.

*Mature cane diameter.*—'Beaufort' — 3.2 cm. 'Reveille' — 4.4 cm. 'Pamlico' — 3.1 cm. 'Lenoir' — 4.2 cm. 'Carteret' — 4.4 cm.

*Mature cane length.*—'Beaufort' — 1.1 m. 'Reveille' — 1.1 m. 'Pamlico' — 1.0 m. 'Lenoir' — 1.1 m. 'Carteret' — 1.1 m.

*Internode length on first flush growth.*—'Beaufort' — 10.0 cm. 'Reveille' — 7.5 cm. 'Pamlico' — 8.0 cm. 'Lenoir' — 9.0 cm. 'Carteret' — 13.0 cm.

*Number of renewal stems.*—'Beaufort' — 1.0. 'Reveille' — 0.50. 'Pamlico' — 2.0. 'Lenoir' — 2.0. 'Carteret' — 1.0.

*Dormant mature stem color.*—Gray-brown (RHS 199C) for 'Beaufort', 'Reveille', 'Pamlico' and 'Carteret'. Gray-brown (RHS 199C–199D) for 'Lenoir'.

*Dormant one year stem color.*—'Beaufort' — red (RHS 46A) on the exposed surface, yellow-orange (RHS 22A) on the unexposed surface. 'Reveille' — red (RHS 46A) on all surfaces. 'Pamlico' — red (RHS 46B) on the exposed surface, yellow-green (RHS 146C) on the unexposed surface. 'Lenoir' — red (RHS 46A) on the exposed surface, yellow-green (RHS 146C–147C) on the unexposed surface. 'Carteret' — red (RHS 46A) on all surfaces.

*First flush growth stem color in summer.*—'Beaufort' — yellow-green (RHS 145B). 'Reveille' — green (RHS 138C). 'Pamlico' — yellow-green (RHS 145B). 'Lenoir' — yellow-green (RHS 147C). 'Carteret' — yellow-green (RHS 145A).

*Pubescence on summer and one year dormant stems.*—No stem pubescence on 'Beaufort', 'Reveille', 'Pamlico', 'Lenoir', or 'Carteret'.

Leaves:

*Leaf blade dimensions.*—'Beaufort' — length 66 mm, width 29 mm, L/W ratio 2.28. 'Reveille' — length 44 mm, width 20 mm, L/W ratio 2.20. 'Pamlico' — length 60 mm, width 22 mm, L/W ratio 2.73. 'Lenoir' — length 61 mm, width 33 mm, L/W ratio 1.85. 'Carteret' — length 61 mm, width 35 mm, L/W ratio 1.74.

*Leaf petiole length.*—'Beaufort' — 4 mm. 'Reveille' — 2 mm. 'Pamlico' — 4 mm. 'Lenoir' — 3 mm. 'Carteret' — 4 mm.

*Leaf shape.*—'Beaufort' — narrowly elliptic. 'Reveille' — narrowly elliptic to narrowly elliptic-obovate. 'Pamlico' — narrowly elliptic. 'Lenoir' — elliptic to elliptic obovate. 'Carteret' — elliptic-obovate to elliptic.

*Leaf apex angle.*—Acute for 'Beaufort', 'Reveille', 'Pamlico' and 'Carteret'. Acuminate for 'Lenoir'.

*Leaf base angle.*—Acute for 'Beaufort', 'Reveille', 'Pamlico', 'Lenoir' and 'Carteret'.

*Leaf margin.*—Entire for 'Beaufort', 'Reveille', 'Pamlico' and 'Lenoir'. Mainly entire, but with occasional irregular serrulations for 'Carteret'.

*Leaf pubescence.*—None for 'Beaufort', 'Reveille', 'Pamlico', 'Lenoir' and 'Carteret'.

*Leaf glands.*—None for 'Beaufort', 'Reveille', 'Pamlico', 'Lenoir' and 'Carteret'.

*Leaf color.*—The adaxial surface color is green (RHS 139A) and the abaxial color green (RHS 138C) for 'Beaufort' and 'Reveille'. The adaxial leaf surface color is green (RHS 137A–137B) and the abaxial surface color also green (RHS 138B) for 'Carteret' and 'Pamlico'. The adaxial surface color is green (RHS 137A) and the abaxial color green (RHS 138B) for 'Lenoir'.

Flowers:

*Number of petals.*—Five, fused into a corolla tube.

*Number of flowers per inflorescence.*—'Beaufort' — 3.0. 'Reveille' — 4.0. 'Pamlico' — 5.0. 'Lenoir' — 5.0. 'Carteret' — 5.5.

*Flower dimensions.*—'Beaufort', 'Pamlico', 'Lenoir' and 'Carteret' — length 9.0 mm, diameter 5.0 mm, L/D ratio 1.8. 'Reveille' — length 9.0 mm, diameter 7.0 mm, L/D ratio 1.3.

*Length of the single style.*—'Beaufort' and 'Carteret' — 8.0 mm. 'Reveille', 'Pamlico' and 'Lenoir' — 9.0 mm.

*Flower shape.*—'Beaufort', 'Pamlico', 'Lenoir' and 'Carteret' — cylindro-urceolate. 'Reveille' — urceolate.

*Flower color.*—'Beaufort' — white (RHS 155D) just prior to opening and on fully open flowers. 'Carteret' — red-purple (RHS 73C) on the fused petal lobes just prior to opening, fading to all white (RHS 155D) on fully open flowers. 'Reveille' — red-purple (RHS 63B) on the exposed side and all lobes of the flowers just prior to opening, fading to all white (RHS 155B) on fully open flowers. 'Pamlico' — red-purple (RHS 62D) on the basal half of the flowers just prior to opening, fading to all white (RHS 155D) on fully open flowers. 'Lenoir' — red-purple (RHS 62C) on the basal half of flowers just prior to opening, fading to all white (RHS 155C) on fully open flowers.

Fruit:

*Fruit dimensions.*—'Beaufort' — length 13 mm, diameter 16 mm, L/D ratio 0.81. 'Reveille' — length 15 mm, diameter 16 mm, L/D ratio 0.94. 'Pamlico' — length 13 mm, diameter 15 mm, L/D ratio 0.87. 'Lenoir' — length 12 mm, diameter 17 mm, L/D ratio 0.71. 'Carteret' — length 15 mm, diameter 18 mm, L/D ratio 0.83.

*Fruit shape.*—'Beaufort' — round-oblate. 'Reveille' — round. 'Pamlico' — round-oblate. 'Lenoir' — oblate. 'Carteret' — round-oblate.

*Fruit pedicel length.*—'Beaufort' — 7 mm. 'Reveille' — 4 mm. 'Pamlico' — 6 mm. 'Lenoir' — 8 mm. 'Carteret' — 4 mm.

*Fruit picking scar.*—'Beaufort' — 1.5 mm diameter, dry. 'Reveille' — 1.0 mm diameter, dry. 'Pamlico' — 1.0 mm diameter, dry. 'Lenoir' — 2.0 mm diameter, dry. 'Carteret' — 1.0 mm diameter, dry.

*Fruit calyx orientation and prominence.*—Appressed against the apical end of the fruit and not prominent for 'Beaufort', 'Reveille' and 'Lenoir'. Perpendicular (protruding) and prominent for 'Carteret' and 'Pamlico'.

*Fruit color with bloom* (*epicuticular wax*).—'Beaufort' — violet-blue (RHS 97C) (FIG. 2). 'Reveille' — violet-blue (RHS 97B–97C)). 'Pamlico' — violet-blue (RHS 97D). 'Lenoir' — violet-blue (RHS 97B). 'Carteret' — violet-blue (RHS 97C).

*Fruit color without bloom.*—Black (RHS 202A) for 'Beaufort', 'Reveille', 'Pamlico', 'Lenoir' and 'Carteret'.

Seeds:

*Number of fully developed seeds per berry.*—'Beaufort' — 44. 'Reveille' — 36. 'Pamlico' — 29. 'Lenoir' — 22. 'Carteret' — 32.

*Seed dimensions.*—'Beaufort' — length 1.25 mm, width 1.00 mm, L/W ratio 1.2. 'Reveille' — length 1.25 mm, width 1.00 mm, L/W ratio 1.2. 'Pamlico' — length 1.50 mm, width 1.00 mm, L/W ratio 1.5. 'Lenoir' — length 1.50 mm, width 0.75 mm, L/W ratio 2.0. 'Carteret' — length 1.50 mm, width 1.00 mm, L/W ratio 1.5.

*Seed shape.*—Basically depressed-ovate for 'Beaufort', 'Reveille', 'Pamlico', 'Lenoir' and 'Carteret'. The technical (pomological) descriptive data comparing 'Beaufort' to 'Reveille', 'Pamlico', 'Lenoir' and 'Carteret' at Castle Hayne, N.C., is presented in Tables 2–7, except for time of flowering, where the data was more representative from Jackson Springs, N.C., in 1992 (Table 1).

Time of flowering.—'Beaufort' was identical to 'Carteret', 'Reveille' and 'Pamlico' for date of first bloom, and very similar to 'Reveille' and 'Lenoir' for 50% bloom date (Table 1). It was 11 days earlier than 'Lenoir' for date of first bloom. It was later than 'Carteret' and 'Pamlico' for 50% bloom date.

TABLE 1

Time of flowering of blueberry cultivars at Jackson Springs, NC, in 1992.

| Cultivar | Date of first bloom | Date of 50% bloom |
|---|---|---|
| 'Carteret' | 3/12 | 4/1 |
| 'Reveille' | 3/12 | 4/9 |
| 'Pamlico' | 3/12 | 4/3 |
| 'Lenoir' | 3/23 | 4/11 |
| 'Beaufort' | 3/12 | 4/10 |

Pollination requirements: The flowers of 'Beaufort' are not self-fertile and require cross-pollination to set commercial crops of fruit. The varieties 'Blue Ridge' (unpatented) and 'Pender' have been identified as being suitable pollinators for 'Beaufort'.

Pollen production: 'Beaufort' flowers produce abundant pollen.

Season of ripening: With regard to ripening season, 'Beaufort' ripens in late midseason, following 'Pamlico', 'Carteret' and 'Lenoir' (Table 2), therefore it completes a series of fresh market mechanical harvest adapted blueberry varieties developed by North Carolina State University that range from very early ripening ('Reveille'), early ('Craven'), early to early midseason ('Pamlico'), early midseason ('Carteret'), early midseason to midseason ('Lenoir') and late midseason ('Beaufort').

TABLE 2

Season of ripening for blueberry cultivars at Castle Hayne, NC.

| | Cumulative percent ripe by June eighth[1] | | | |
|---|---|---|---|---|
| Cultivar | 1999 | 2000 | 2001 | Average |
| 'Carteret' | 38 | 74 | 43 | 52 |
| 'Reveille' | 79 | 100 | 91 | 90 |
| 'Pamlico' | 38 | 74 | 43 | 52 |
| 'Lenoir' | 38 | 70 | 43 | 50 |
| 'Beaufort' | 29 | 55 | 33 | 39 |

[1]Percent ripe after the first two weeks of the season.

Yield per plant: Yield of 'Beaufort' was equal to all varieties except 'Carteret' in 1999 and 2001 (Table 3). Average yield across all three years was higher than 'Reveille'.

TABLE 3

Yield of blueberry cultivars at Castle Hayne, NC.

| | Yield (lbs./plant)[1] | | | |
|---|---|---|---|---|
| Cultivar | 1999 | 2000[2] | 2001 | Average |
| 'Carteret' | 14.0a | 3.3bc | 14.3a | 10.5 |
| 'Reveille' | 5.9cd | 2.4c | 8.8c | 5.7 |
| 'Pamlico' | 7.7bcd | 4.6a | 11.6ab | 8.0 |
| 'Lenoir' | 5.9cd | 4.4ab | 12.5ab | 7.6 |
| 'Beaufort' | 8.6bc | 3.3bc | 10.8bc | 7.5 |

[1]Values not followed by the same letter(s) are significantly different at the 0.05 level (Duncan's Multiple Range Test).
[2]Yield adversely affected by harvest method (catch frames and rubber hoses).

Fruit size (weight per berry): There were few differences between 'Beaufort' and the other four varieties for fruit size (Table 4). This is not surprising since all were originally selected for adaptation to mechanical harvest for the fresh market, which dictates that the fruit size be modest to minimize damage to the fruit during the harvesting process.

TABLE 4

Fruit size of blueberry cultivars at Castle Hayne, NC.

| | Fruit size (weight per berry in grams)[1] | | | |
|---|---|---|---|---|
| Cultivar | 1999 | 2000 | 2001 | Average |
| 'Carteret' | 1.22 | 1.30 | 1.15abc | 1.22 |
| 'Reveille' | 1.31 | 1.27 | 1.14abc | 1.24 |
| 'Pamlico' | 1.27 | 1.25 | 0.96cd | 1.16 |
| 'Lenoir' | 1.34 | 1.22 | 1.12bc | 1.23 |
| 'Beaufort' | 1.26 | 1.27 | 1.10bcd | 1.21 |

[1]Values not followed by the same letter(s) are significantly different at the 0.05 level (Duncan's Multiple Range Test).

Fruit color: In addition to The Royal Horticultural Society Colour Chart, fruit color was also determined objectively with a Minolta Color Meter (Table 5), and these data indicated that 'Beaufort' was at least equal to all varieties with which it was compared except 'Pamlico'. 'Beaufort' fruit color was superior to 'Lenoir' in this comparison.

TABLE 5

Fruit color and fruit firmness of blueberry cultivars at Castle Hayne, NC.

| | Color[1, 2] | Firmness[1, 3] | |
|---|---|---|---|
| Cultivar | 2001 | 1999 | 2001 |
| 'Carteret' | 18.1cd | 118c | 144d |
| 'Reveille' | 20.2abc | 173a | 216a |
| 'Pamlico' | 22.6a | 124c | 172c |
| 'Lenoir' | 14.1d | 124c | 176bc |
| 'Beaufort' | 18.8bc | 142b | 190b |

[1]Values not followed by the same letter(s) are significantly different at the 0.05 level (Duncan's Multiple Range Test).
[2]Color (lightness or "L" values) determined objectively by a Minolta Color Meter. Higher values indicate lighter blue color.
[3]Fruit firmness determined objectively using a Firm-tech Firmness Tester.

Fruit firmness: Fruit firmness determined by a Firm-tech Firmness Tester demonstrated that 'Beaufort' was superior to 'Carteret', 'Pamlico' and 'Lenoir' in 1999 (Table 5). It was equal to 'Lenoir' and superior to 'Carteret' and 'Pamlico' in 2001. It was not as firm as the very firm variety 'Reveille' in either year. 'Beaufort' fruit definitely is sufficiently firm to deem this variety adapted to mechanical harvest for the fresh market.

Fruit flavor: Subjective ratings for flavor indicated that 'Beaufort' consistently scored in the superior to very good range (Table 6), and fruit quality is definitely one of this variety's strong points.

TABLE 6

Fruit flavor of blueberry cultivars at Castle Hayne, NC.

| Cultivar | Flavor[1, 2] 1999 | 2000 | 2001 |
|---|---|---|---|
| 'Carteret' | 79a | 72f | 78bc |
| 'Reveille' | 80a | 79a | 80a |
| 'Pamlico' | 76b | 74e | 79ab |
| 'Lenoir' | 75b | 76bcd | 79ab |
| 'Beaufort' | 80a | 78ab | 79ab |

[1]Values not followed by the same letter(s) are significantly different at the 0.05 level (Duncan's Multiple Range Test).

[2]Subjective ratings based on a 0-90 scale, where less than 60 is unsatisfactory, 60-69 is satisfactory, 70-79 is average to good, and 80 and above superior.

Post harvest shelf-life: Post harvest shelf-life of fruit is not one of the strongest characteristics of 'Beaufort' (Table 7). However, after 50° F. storage for seven days the percent marketable fruit was only 10% less than 'Carteret' so it was acceptable. The prevailing higher temperatures during the ripening season for 'Beaufort' (late midseason) probably contribute significantly to reduced shelf-life potential.

TABLE 7

Post harvest shelf-life of the fruit of blueberry cultivars at Castle Hayne, NC, in 2001.

| Cultivar | Percent marketable fruit after seven days[1] 50° F. | 70° F. |
|---|---|---|
| 'Carteret' | 62b | 44a |
| 'Reveille' | 81a | 48a |
| 'Pamlico' | 77a | 38a |
| 'Lenoir' | 83a | 44a |
| 'Beaufort' | 52c | 8b |

[1]Values not followed by the same letter(s) are significantly different at the 0.05 level (Duncan's Multiple Range Test).

Propagation: 'Beaufort' is easily propagated asexually by both hardwood and softwood stem cuttings.

Chilling requirement: The chilling requirement of 'Beaufort' flower and leaf buds is between 600 and 800 hours below 45° F.

Disease reaction: 'Beaufort' has not had any problems with either of the two major diseases affecting blueberries in North Carolina, stem canker (*Botryosphaeria corticis*) and stem blight (*Botryospheria dothidea*).

That which is claimed is:

1. A new and distinct variety of commercial blueberry (*Vaccinium corymbosum* Linnaeus) plant substantially as illustrated and described, characterized by its late midseason ripening, high yields, good picking scar, very good fruit quality, color and firmness, small to medium fruit size, and adaptation to mechanical harvest for fresh fruit market outlets.

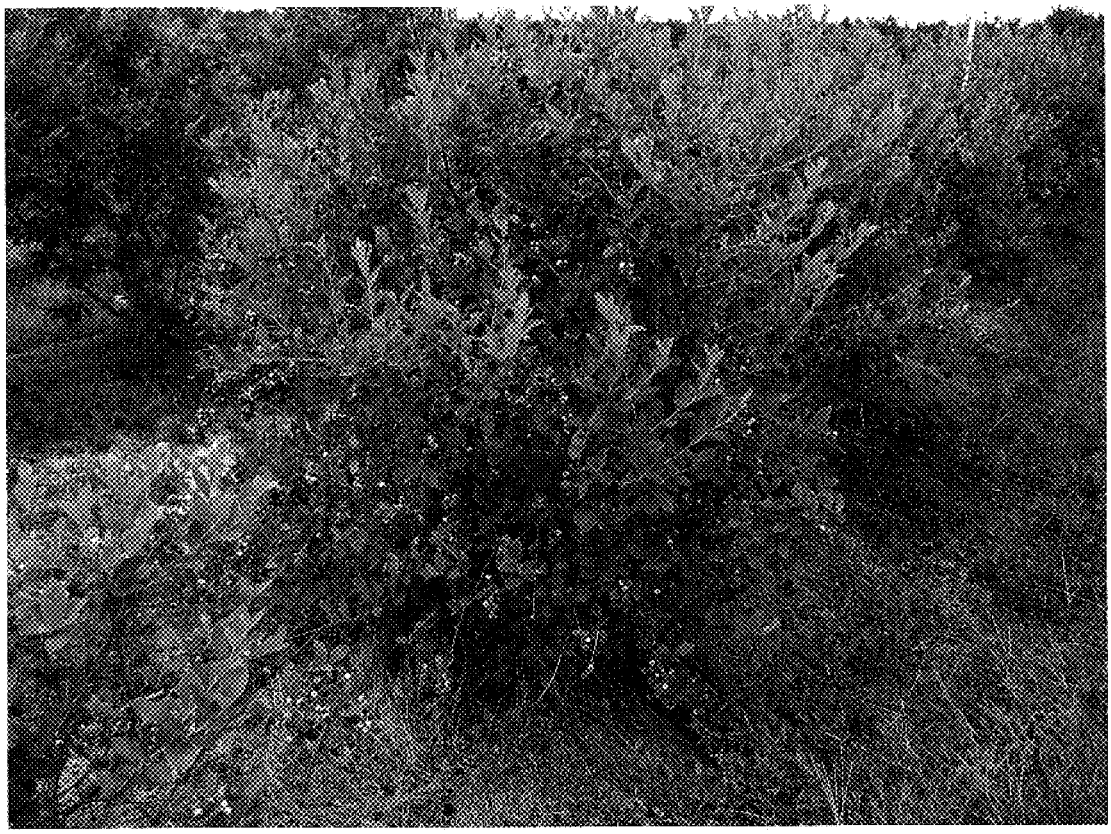

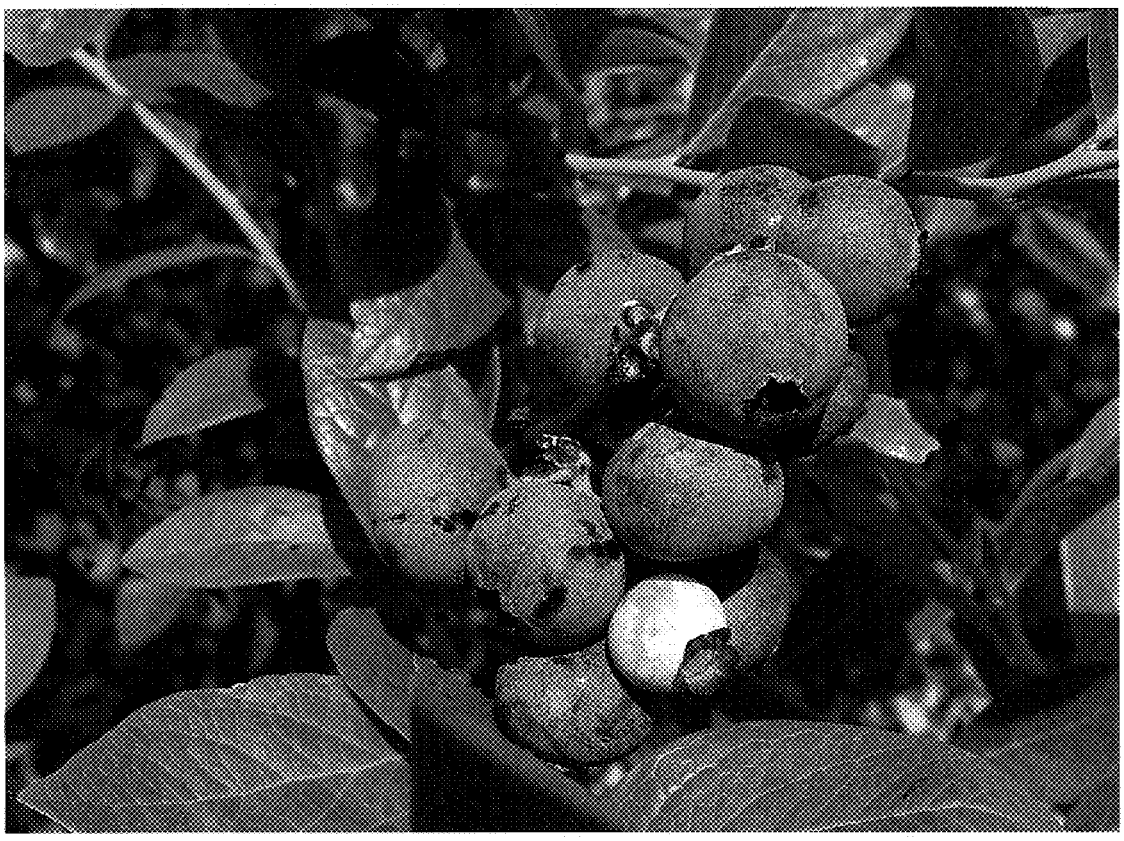

* * * * *